(12) United States Patent
Angeletakis

(10) Patent No.: US 7,625,551 B2
(45) Date of Patent: Dec. 1, 2009

(54) POLYETHER-BASED DENTAL IMPRESSION MATERIAL CURABLE BY METATHESIS REACTION

(75) Inventor: Christos Angeletakis, Orange, CA (US)

(73) Assignee: Kerr Corporation, Orange, CA (US)

( * ) Notice: Subject to any disclaimer, the term of this patent is extended or adjusted under 35 U.S.C. 154(b) by 604 days.

(21) Appl. No.: 11/276,273

(22) Filed: Feb. 21, 2006

(65) Prior Publication Data

US 2006/0173091 A1 Aug. 3, 2006

Related U.S. Application Data

(63) Continuation-in-part of application No. 10/988,881, filed on Nov. 15, 2004, now Pat. No. 7,001,590.

(51) Int. Cl.
*A61K 7/16* (2006.01)
*C08L 83/05* (2006.01)
*C08L 5/24* (2006.01)
*C08L 3/34* (2006.01)

(52) U.S. Cl. .......................... 424/49; 523/107; 523/109; 524/264; 524/448

(58) Field of Classification Search .................. 424/49; 523/107, 109; 524/264, 448
See application file for complete search history.

(56) References Cited

U.S. PATENT DOCUMENTS

| | | | |
|---|---|---|---|
| 4,584,425 | A | 4/1986 | Tom |
| 4,717,498 | A | 1/1988 | Maxon |
| 4,849,127 | A | 7/1989 | Maxon |
| 5,198,511 | A | 3/1993 | Brown-Wensley et al. |
| 5,266,670 | A | 11/1993 | Nakos et al. |
| 5,296,566 | A | 3/1994 | Brown-Wensley et al. |
| 5,312,881 | A | 5/1994 | Marks et al. |
| 5,330,948 | A | 7/1994 | Marks et al. |
| 5,455,317 | A | 10/1995 | Marks et al. |
| 5,491,206 | A | 2/1996 | Brown-Wensley et al. |
| 5,728,785 | A | 3/1998 | Grubbs et al. |
| 5,831,108 | A | 11/1998 | Grubbs et al. |
| 5,939,504 | A | 8/1999 | Woodson, Jr. et al. |
| 5,942,638 | A | 8/1999 | Lichtenhan et al. |
| 6,001,909 | A | 12/1999 | Setiabudi |
| 6,040,363 | A | 3/2000 | Warner et al. |
| 6,071,459 | A | 6/2000 | Warner et al. |
| 6,075,068 | A | 6/2000 | Bissinger |
| 6,077,805 | A | 6/2000 | Van Der Schaaf et al. |
| 6,121,362 | A | 9/2000 | Wanek et al. |
| 6,252,101 | B1 | 6/2001 | Herzig et al. |
| 6,306,987 | B1 | 10/2001 | Van Der Schaaf et al. |
| 6,310,121 | B1 | 10/2001 | Woodson, Jr et al. |
| 6,323,295 | B1 | 11/2001 | Muhlebach et al. |
| 6,323,296 | B1 | 11/2001 | Warner et al. |
| 6,403,522 | B1 | 6/2002 | Bolm et al. |
| 6,407,190 | B1 | 6/2002 | Van Der Schaaf et al. |
| 6,409,875 | B1 | 6/2002 | Giardello et al. |
| 6,410,666 | B1 | 6/2002 | Grubbs et al. |
| 6,417,363 | B1 | 7/2002 | Van Der Schaaf et al. |
| 6,455,029 | B1 | 9/2002 | Angeletakis et al. |
| 6,465,554 | B1 | 10/2002 | Van Der Schaaf et al. |
| 6,518,356 | B1 | 2/2003 | Friese et al. |
| 6,521,799 | B2 | 2/2003 | Wagener et al. |
| 6,525,125 | B1 | 2/2003 | Giardello et al. |
| 6,620,955 | B1 | 9/2003 | Pederson et al. |
| 6,649,146 | B2 | 11/2003 | Angeletakis et al. |
| 6,794,534 | B2 | 9/2004 | Grubbs et al. |
| 6,818,586 | B2 | 11/2004 | Grubbs et al. |
| 6,921,735 | B2 | 7/2005 | Hoveyda et al. |
| 7,001,590 | B1 | 2/2006 | Angeletakis |
| 2002/0153096 | A1 | 10/2002 | Giardello et al. |
| 2002/0185630 | A1 | 12/2002 | Piccinelli et al. |
| 2004/0225073 | A1 | 11/2004 | Angeletakis |
| 2005/0159510 | A1 | 7/2005 | Smolak et al. |
| 2005/0182218 | A1 | 8/2005 | Liaw et al. |

FOREIGN PATENT DOCUMENTS

| | | |
|---|---|---|
| DE | 19859191 A1 | 6/2000 |
| EP | 0796607 A2 | 9/1997 |
| EP | 0771830 A2 | 12/1999 |
| EP | 1025830 A2 | 8/2000 |
| EP | 0940405 A1 | 6/2001 |
| EP | 1241196 A2 | 9/2002 |
| EP | 1555290 A1 | 7/2005 |
| EP | 1656924 A1 | 5/2006 |
| JP | 2001002719 A | 1/2001 |
| JP | 2002284789 A | 10/2002 |
| WO | WO9839346 A1 | 11/1998 |
| WO | WO9900396 A1 | 1/1999 |
| WO | WO9900397 A1 | 1/1999 |
| WO | WO9929701 A1 | 6/1999 |
| WO | WO9950330 A2 | 10/1999 |
| WO | WO9960030 A1 | 11/1999 |
| WO | WO0046255 A1 | 8/2000 |
| WO | WO0232338 A2 | 4/2002 |
| WO | WO03093351 A1 | 11/2003 |

OTHER PUBLICATIONS

European Patent Office, European Search Report, Mar. 13, 2006, 5 pp.

(Continued)

*Primary Examiner*—Robert D. Harlan
(74) *Attorney, Agent, or Firm*—Wood, Herron & Evans, LLP

(57) ABSTRACT

Two-part dental impression material curable by a metathesis reaction comprising a base paste with first and second resin components each containing at least two cycloolefin groups per molecule curable by a metathesis reaction with a metathesis catalyst. The first resin includes a urethane polyether or polyester carboxylate backbone terminated with the cycloolefin groups and the second resin includes an alkoxysiloxane polyether or polyester carboxylate backbone terminated with the cycloolefin groups. The metathesis catalyst can be a ruthenium carbene complex catalyst.

20 Claims, No Drawings

OTHER PUBLICATIONS

European Patent Office, Search Report and Written Opinion for related EP Patent Application No. 07250732.0, dated Jul. 5, 2007, 6 pgs.

International Organization for Standardization, Dental elastomeric impression materials; ISO 4823 (1992).

Scholl et al., Synthesis and activity of a new generation of ruthenium-based olefin metathesis catalysts coordinated with 1,3-dimesityl-4,5-dihydroimidazol-2-ylidene ligands, Org. Lett., vol. 1, No. 6, 953-956 (1999).

Chevalier et al., Ring-opening olefin metathesis polymerisation (ROMP) as a potential cross-linking mechanism for siloxane polymers, J. of Inorganic and Organometallic Polymers, vol. 9, No. 3, 151-164 (1999).

L. LeCamp et al., Polydimethyl siloxane photoreticulable par vole cationique-I, Eur. Polym. J., vol. 33, No. 9, 1453-1462 (1997).

Kim et al., Surface-initiated ring-opening metathesis polymerization on Si/SiO2, Macromolecules 2000, 33(8), 2793-2795 (2000).

POLYETHER-BASED DENTAL IMPRESSION MATERIAL CURABLE BY METATHESIS REACTION

CROSS REFERENCE TO RELATED APPLICATIONS

This application is a continuation-in-part of co-pending, commonly-owned U.S. Pat. No. 7,001,590, the disclosure of which is incorporated herein by reference in its entirety as if completely set forth herein below. This application is also related to co-pending, commonly-owned U.S. patent application Ser. No. 10/430,590 filed May 6, 2003, entitled METHOD OF CURING A COMPOSITION BY METATHESIS REACTION USING REACTION CONTROL AGENT, and to commonly-owned U.S. patent application Ser. No. 11/276,270 filed on even date herewith entitled POLYETHER-BASED COMPOSITION CURABLE BY METATHESIS REACTION, the disclosures of which are incorporated herein by reference in their entirety as if completely set forth herein below.

FIELD OF THE INVENTION

This invention relates to polyether-based dental impression materials that undergo a metathesis reaction initiated by a metathesis catalyst. More specifically, the invention relates to dental impression materials formed by ring opening metathesis polymerization (ROMP) of functionalized polyether urethane carboxylates and functionalized alkoxy-siloxane polyether carboxylates catalyzed with metal carbene complexes.

BACKGROUND OF THE INVENTION

Several types of thermoset polymers are generally used in commerce. One type is the acrylic thermoset polymers cured by a free radical addition mechanism. These polymers are cured by heat initiators, such as peroxides, or by photoinitiators, such as alpha diketones. A characteristic of the cured acrylates, however, is large polymerization shrinkage, which is undesirable for many uses. Another undesirable characteristic of acrylates is the formation of an oxygen-inhibited layer on the surface upon curing.

Another type of thermoset polymers is the one based on cationic polymerization of oxirane (epoxy) monomers. These are cured by use of a two-part system or by use of photoinitiators. The disadvantages of oxirane-derived polymers, however, are high water uptake in service, large polymerization shrinkage, and high cost.

Another type of thermoset polymers is the one based on a ring-opening metathesis polymerization (ROMP) mechanism. Metathesis is generally understood to mean the metal catalyzed redistribution of carbon-carbon double bonds. The polymerizable composition comprises a resin system that includes functionalities or groups that are curable by ROMP together with a metathesis catalyst, such as a ruthenium carbene complex. In addition to ROMP, other metathesis reaction systems utilize metathesis catalysts, for example ring closing metathesis, acyclic diene metathesis polymerization, ring opening metathesis and cross metathesis.

The thermoset monomer types that are curable by ROMP are the cycloolefins, such as dicyclopentadiene (DCPD), as described in Woodson U.S. Pat. No. 6,310,121. Various other patents address the polymerization of cyclic olefins such as DCPD, tricyclododecene and the like, for example, Tom U.S. Pat. No. 4,584,425. Two of these patents mention compounds containing norbornenyl functional groups and ROMP with the goal of producing a highly crosslinked polymer, namely Bissinger U.S. Pat. No. 6,075,068 and EP 1025830A2 by Moszner. Bissinger describes several ROMP catalyzed resin systems based on dinorbornenyl dicarboxylate ester (DNBDE) compounds or a combination of DNBDE compounds and acrylates. A trinorbornenyl tricarboxylate ester (TNBTE) compound was also disclosed. Moszner describes ROMP of norbornenyl monocarboxylate, which is a monofunctional monomer. However, the combination of the particular resins and catalysts does not achieve the controlled reaction progress desired for many applications.

In dentistry, addition silicones are the most widely used impression materials. Addition silicones cure with a hydrosilation mechanism and contain a platinum compound as a catalyst. Despite the addition of various surfactants, the hydrophilicity of the materials as measured by contact angle measurements, especially before set is completed, is very low. This reduces the ability of the impression material to displace oral fluids during curing and results in a compromised impression. Another class of impression material, the polyethers, as exemplified by IMPREGUM® (from 3M ESPE) are 2-part systems containing imine terminated polyether copolymers cured by reaction with a strong acid. However, these polyethers suffer from high rigidity, which is a property of crosslinked polyethers, and poor taste and smell due to the presence of imines and strong acids.

There is thus a need for a polyether-based impression material with improved flexibility, taste and smell.

SUMMARY OF THE INVENTION

The present invention provides a two-part dental impression material comprising a base paste and a catalyst paste that upon mixing the pastes undergoes a metathesis reaction, such as ring-opening metathesis polymerization (ROMP). The two-part compositions of the present invention comprise, in the base paste, a first base resin and a second base resin, each containing at least two cycloolefin groups capable of undergoing a metathesis reaction. By way of example, the cycloolefinic groups may be norbornenyl, norbornenylethyl, cyclopentenyl, 7-oxanorbornenyl, norbornadienyl, and/or 7-oxanorbornadienyl. The functional cycloolefin groups may be pendant, terminal or cyclic groups.

The first base resin has the formula:

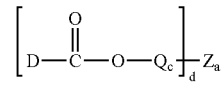

wherein:

a=1-100, c=0 or 1 and d=2-100,

Q is a linear, branched, cyclic or polycyclic organic residue optionally containing siloxane groups (Si—O—Si) and optionally containing heteroatoms selected from the group consisting of B, N, O, Si, P, and S, Z is a linear, branched, cyclic or polycyclic urethane polyether or urethane polyester optionally containing siloxane groups (Si—O—Si) and optionally containing heteroatoms selected from the group consisting of B, N, O, Si, P, and S, and D is a cycloolefinic residue and is different than Q or Z. By way of example, the first base resin may be a dinorbornenyl dicarboxylate urethane polyether or polyester. In one embodiment, the first base resin has the following structure:

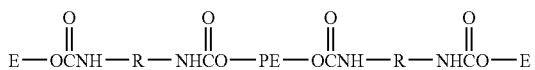

where E=a cycloolefinic endcapper, R=a diisocyanate fragment, and PE=a polyol. In a further embodiment, R may be hexyl, PE may be a polyether, and E may have the following structure:

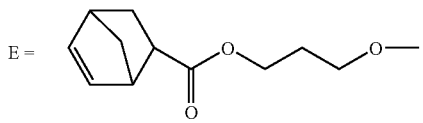

The second base resin has the formula:

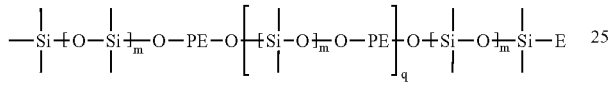

wherein:

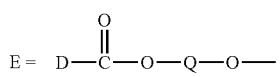

PE is a polyether or polyester fragment,
m=1-500,
q=0-10,

Q is a linear, branched, cyclic or polycyclic organic residue optionally containing siloxane groups (Si—O—Si) and optionally containing heteroatoms selected from the group consisting of B, N, O, Si, P, and S, and D is a cycloolefinic residue and is different than Q or Z. In one embodiment, the second base resin may be an alkoxysiloxane polyether norbornenecarboxylate. In another embodiment, PE is a polyether, m=1-50, q is 0-1, and E=a cycloolefinic endcapper. In a further embodiment, E may have the following structure:

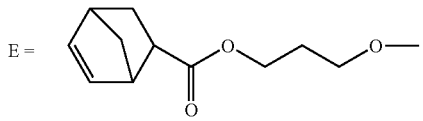

In one embodiment of the present invention, the base paste may further comprise a third base resin that is a siloxane carboxylate backbone functionalized with cycloolefin groups capable of undergoing a metathesis reaction. The functional cycloolefin groups in the third base resin may be pendant, terminal or cyclic groups. In one embodiment, the third base resin is at least one of:

a pendant structure having the following formula:

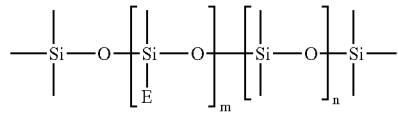

a terminated structure having the following formula:

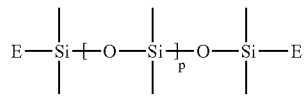

or
a cyclic structure having the following formula:

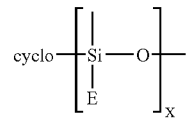

where m=1-50, n=0-200, p=0-200, x=3-6 and E is a cycloolefinic residue.

In the two-part dental impression materials of the present invention, the catalyst paste contains the metal carbene complex catalyst, which upon mixing of the catalyst paste with the base paste, initiates the metathesis reaction of the base resins. The catalyst may have the following structure:

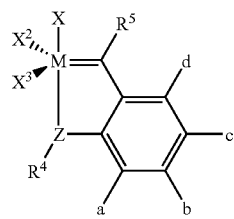

wherein:
  M is ruthenium or osmium,
  X is an alkylidene ligand with basicity higher than that of tricyclohexylphosphine ($PCy_3$),
  $X^2$ and $X^3$ are either the same or different and are any anionic ligand,
  Z is oxygen (O) or sulfur (S), and
  $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

In an embodiment of the present invention, the base paste and the catalyst paste each further comprise a plasticizer (solvent) and/or a filler system. In one embodiment, the base paste includes a hydrophilic filler. In another embodiment, the catalyst paste includes a hydrophobic filler.

DETAILED DESCRIPTION

The present invention provides dental impression material formulations of ruthenium or osmium carbene complexes together with base resins that include cycloolefin groups curable by a metathesis reaction, as a two-part (catalyst-base) system. The compositions of the present invention may also contain fillers, plasticizers (solvents) and other additives, such as pigments or surfactants, for performance improvement. As used herein, the term "base," "base resin" or "base component" refers to the chief component(s) or active ingredient(s) that undergo(es) the metathesis reaction, which in the present invention are resins containing functional cycloolefin groups. A "base resin" is a resin that contains that chief component. The term "base paste" refers to the paste in a paste-paste (two-part) composition that contains the chief component(s), while the other paste, the catalyst paste, contains the catalyst that initiates the metathesis reaction of the chief component(s) upon mixing of the two pastes.

In the two-part (base-catalyst) composition of the present invention, the metathesis catalyst is pre-dissolved in a suitable fluid, such as a citric acid ester plasticizer (solvent), to form a catalyst paste. The base paste contains at least a first base resin and a second base resin, each having at least two cycloolefin groups, such as cycloalkenyl groups, per molecule. The functional cycloolefin groups may be pendant, terminal or cyclic groups. By "terminal," it is meant that the backbone is terminated at the ends with functional groups. These "terminal groups" may also be referred to herein as "end groups" or "endcappers." The first base resin may be, for example, a difunctional or trifunctional urethane polyether or polyester carboxylate containing cycloolefin groups, such as norbornenyl end groups. The base paste also may optionally contain a reaction control agent, as disclosed in U.S. Pat. No. 7,001,590, to adjust the work/set time to a desirable level, although the first and second base resins have a tendency in combination to provide good work/set times when catalyzed by ruthenium complex catalysts, such that a reaction control is not likely needed. Upon mixing the two pastes together, the composition undergoes a metathesis reaction initiated by the metathesis catalyst. In an exemplary embodiment, the metathesis reaction proceeds to completion at room and/or body temperature.

In one embodiment of the present invention, the first base resin has the formula:

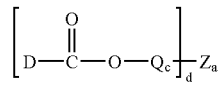

wherein:
a=1-100, c=0 or 1 and d=2-100,

Q is a linear, branched, cyclic or polycyclic organic residue optionally containing siloxane groups (Si—O—Si) and optionally containing heteroatoms selected from the group consisting of B, N, O, Si, P, and S, Z is a linear, branched, cyclic or polycyclic urethane polyether or urethane polyester optionally containing siloxane groups (Si—O—Si) and optionally containing heteroatoms selected from the group consisting of B, N, O, Si, P, and S, and D is a cycloolefinic residue and is different than Q or Z. By way of example, D may be a cycloolefinic residue selected from norbornenyl, norbornenylethyl, cyclopentenyl, 7-oxanorbornenyl, norbornadienyl, and/or 7-oxanorbornadienyl. In one embodiment, the cycloolefin residue has the following structure:

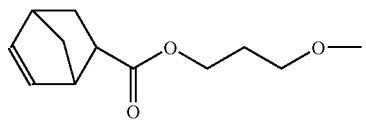

In one further embodiment, d=2-5. In another embodiment, d=2 or 3 such that the first base resin is difunctional or trifunctional. By way of example, Z may be:

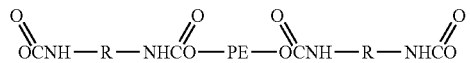

where R=a diisocyanate fragment and PE=a polyol. In a further embodiment, R may be hexyl and PE may be a polyether or polyester. In another embodiment, Z may include a polyether fragment consisting optionally of one or more of butylene oxide units, ethylene oxide units or propylene oxide units, or a combination thereof. As a further example, Z may be a polyester diol consisting of units of a diacid, such as adipic acid, and alkylene oxide units, such as ethylene oxide, propylene oxide and butylene oxide.

A DNBDE may be synthesized via an esterification reaction. As an example, CPD can be reacted with the adduct of hydroxyethyl acrylate with succinic anhydride to give a norbornenyl functional carboxylic acid A. This is followed by esterification of A with polyethylene glycol 400 (PEG 400) using p-toluenesulfonic acid as a catalyst in cyclohexane with azeotropic removal of water to produce Compound 1g as shown in the scheme below.

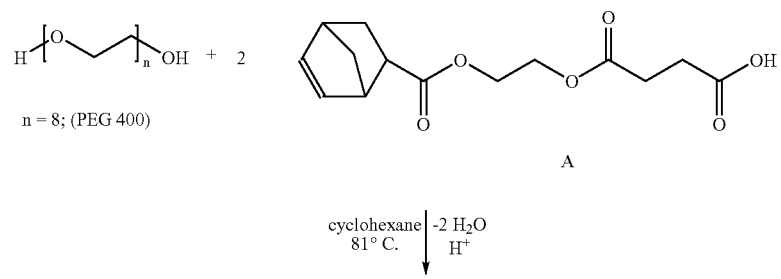

-continued

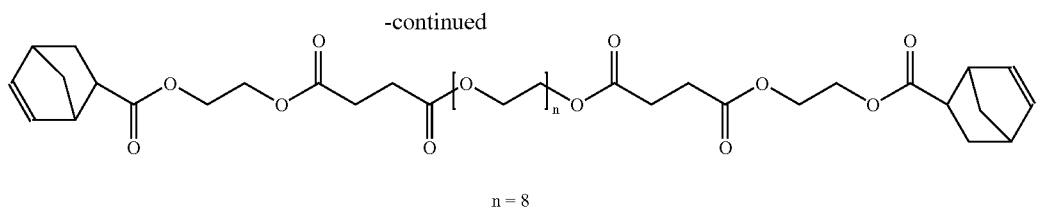

n = 8

When Z is a polyether fragment or a polyester fragment, the resultant polymer after ROMP can be soft and flexible, which makes it desirable for use as a dental impression material. Thus, polyether or polyester diols are used instead of PEG 400, for example, ethylene butylene adipic acid polyester diol such as Desmophen 2000KS from Bayer, diethylene glycol adipic acid polyester diol, and the like. As yet another method, the DNBDE can be made via a transesterification reaction using 5-norbornene-2-carboxylic acid methyl ester and a tin catalyst, as an example; acid or base catalysts can also be used.

However, esterification reactions may not be efficient with relatively high molecular weight polyols, for example, in the analogous situation of the acrylate esters, which are generally not available with polyethylene glycol backbones above 1000 daltons. Acrylate endcapped oligomers, however, are readily available with urethane functionalities via reaction of polyols with isocyanates followed by endcapping with a hydroxyl functional acrylate, such as for example hydroxypropyl acrylate. Analogously norbornenyl group terminated urethane oligomers can be prepared by substituting a hydroxyl functional norbornenylcarboxylate to be used as the endcapper for the hydroxyl functional acrylate. The general structure is shown below:

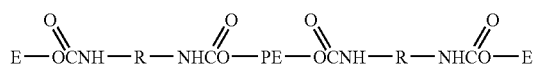

where E=the cycloolefinic endcapper, R=a diisocyanate fragment, and PE=a polyol. In accordance with the present invention then, urethane polyether and polyester oligomers endcapped with norbornenyl groups can thus be prepared for curing using ROMP.

As a first step, an excess of a diisocyanate such as hexane diisocyanate (HDI) was reacted with a polyether diol using a tin catalyst followed by reaction with an endcapper, specifically hydroxypropyl norbornenecarboxylate (HPNBC, E-H in the Scheme below). This endcapper HPNBC was prepared by the reaction of hydroxypropyl acrylate with cyclopentadiene, according to the method discussed in U.S. Pat. No. 7,001,590, incorporated by reference herein. The reaction is shown as follows:

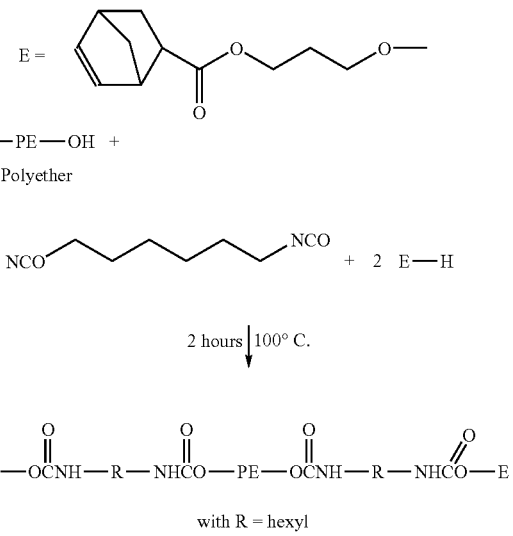

with R = hexyl

The resultant compounds are urethane polyether (UPE) norbornenecarboxylates (terminated with norbornenyl groups). The functional group Z is an adduct of a difunctional polyol with an excess of HDI to afford an isocyanate terminated oligomer. This oligomer reacts with HPNBC to afford a ROMP curable prepolymer.

The second base resin is an alkoxy-siloxane polyether carboxylate backbone functionalized with at least two cycloolefin groups capable of undergoing a metathesis reaction. The second base resin has the formula:

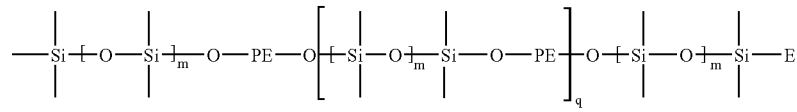

wherein:

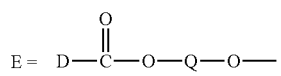

PE is a polyether or polyester fragment,
m=1-500,
q=0-10,

Q is a linear, branched, cyclic or polycyclic organic residue optionally containing siloxane groups (Si—O—Si) and optionally containing heteroatoms selected from the group consisting of B, N, O, Si, P, and S, and D is a cycloolefinic residue and is different than Q or Z. By way of example, D may be a cycloolefinic residue selected from norbornenyl, norbornenylethyl, cyclopentenyl, 7-oxanorbornenyl, norbornadienyl, and/or 7-oxanorbornadienyl. In one embodiment, the cycloolefin residue has the following structure:

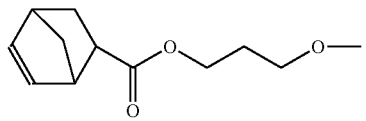

By way of further example, PE is a polyether containing propylene oxide (PO) and ethylene oxide (EO) fragments. In one embodiment of the present invention, PE is a polyether containing PG and EO fragments, m=1-50, q=0-1 and E=a cycloolefinic endcapper. In a further embodiment, m is about 16 and q is 0 or 1. In another embodiment, the second base resin may be an alkoxy-siloxane polyether norbornenecarboxylate.

In an exemplary embodiment of the present invention, the base paste further comprises a third base resin having at least two functional cycloolefin groups that undergo a metathesis reaction, such as ROMP, when mixed with the ruthenium carbene complex. The optional third base resin contains pendant, terminal and/or cyclic cycloolefin groups. The third base resin may be incorporated into the paste, as desired, to reduce the work/set time since they increase cross-linking. In a further exemplary embodiment, the third base resin is added in an amount less than about 20 wt. % of the resin portion of the base paste. The functional cycloolefin groups in the third base resin, for example, can be norbornenyl, norbornenylethyl, cyclopentenyl, 7-oxanorbornenyl, norbornadienyl, and/or 7-oxanorbornadienyl. In one embodiment, the cycloolefin groups have the following structure:

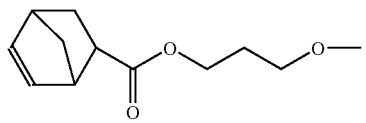

In one embodiment, the third base resin is at least one of: a pendant structure having the following formula:

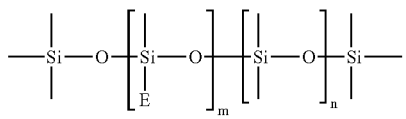

a terminated structure having the following formula:

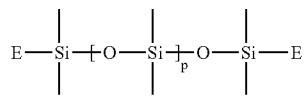

or
a cyclic structure having the following formula:

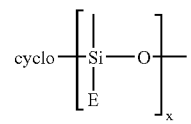

where m=1-50, n=0-200, p=0-200, x=3-6 and E is a cycloolefinic residue. In an exemplary embodiment, the third base resin is a pendant structure. In a further exemplary embodiment, m is about 4 and n is about 20.

The two-part compositions of the present invention contemplate a catalyst paste and base paste that upon mixture with one another, form a curable paste/paste system in which the metathesis reaction proceeds. Generally, in this system, the catalyst paste comprises the metathesis catalyst for initiating polymerization, and a solvent for the catalyst that is miscible or dispersible with the base paste and that does not interfere with the metathesis reaction. The solvent may be a siloxane substituted with alkyl groups and arylalkyl or aryl groups. For example, a citric acid ester can be used, for example, CITROFLEX® A4 from Morflex, Inc. The base paste generally comprises the substrate that is curable via ROMP or other metathesis reaction and optionally a reaction control agent to control the working time.

The catalysts useful in the present invention include ruthenium or osmium carbene complexes, referred to generally as complex 3 catalysts, as shown in the following general structure:

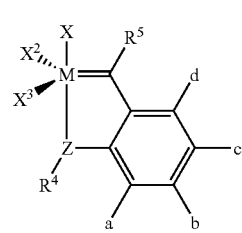

wherein:
M is ruthenium or osmium,
X is an alkylidene ligand with basicity higher than that of tricyclohexylphosphine ($PCy_3$),
Z is oxygen (O) or sulfur (S)
$X^2$ and $X^3$ are either the same or different and are any anionic ligand, and
$R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

In an exemplary embodiment of a complex 3 catalyst, M is ruthenium, X is an alkylidene ligand with basicity higher than that of tricyclohexylphosphine (PCy$_3$), X$^2$ and X$^3$ are halogen atoms, Z is oxygen, R$^4$ is a C$_1$ to C$_{10}$ alkyl fragment, a, b, c and d are either hydrogen or a C$_1$ to C$_{10}$ alkyl or a C$_1$ to C$_{10}$ alkoxy group, and R$^5$ is hydrogen.

In another exemplary embodiment of a complex 3 catalyst, M is ruthenium, X is 1,3-bis(2,4,6-trimethylphenyl)-imidazol-2-ylidene (sIMES), X$^2$ and X$^3$ are chlorine atoms, Z is oxygen, R$^4$ is 2-propyl, a, b, c and d are either hydrogen or methoxy, and R$^5$ is hydrogen. Complex 3-1 is an example of this type of exemplary catalyst for a two-part composition of the present invention. Complex 3-1 is 1,3-bis-(2,4,6-trimethylphenyl)-2-(imidazolidinylidene) dichloro(o-isopropoxyphenylmethylene) ruthenium having the following structure:

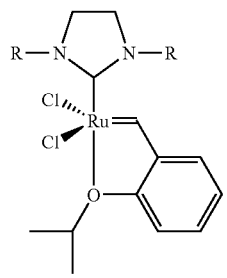

3-1 wherein R is mesityl. The structure may also be shown with an arc between the N atoms in the imidazolidene group to indicate that a double bond is present therebetween, as discussed in U.S. Pat. No. 7,001,590, incorporated by reference herein. The combination of an olefinic resin system and complex 3-1 is believed to provide a highly efficient metathesis reaction system. Other examples for this category of catalysts, as well as the synthesis of these catalysts, are fully described in U.S. Pat. No. 6,921,735, which is incorporated by reference herein in its entirety.

The dental impression material of the present invention may further include a filler system, either in the base paste or the catalyst paste, or both. The fillers useful in the composition of the present invention include reinforcing and/or non-reinforcing (extending) fillers. Suitable reinforcing fillers include precipitated silicas, fumed silica, calcium silicate (Wollastonite), crystalline silica, and the like. The addition of reinforcing filler improves the mechanical strength, such as tensile and tear strengths, of the cured composition. Suitable non-reinforcing fillers include diatomaceous earth, aluminas, magnesias, titanium dioxide, zirconium silicate, calcium carbonate, metallic oxides, and the like. Surface-treated fillers may also be used. Typical surface treatments include silanization and the like. The filler may be present in any amount that imparts the desired consistency and performance, for example, in an amount of about 15 wt. % to about 50 wt. % of the composition.

In one embodiment of the present invention, the base paste includes a reinforcing hydrophilic filler, such as hydrophilic fumed silica. An example of a hydrophilic fumed silica is HDK® N20P commercially available from Wacker Silicones. In a further embodiment, the base paste may also include a non-reinforcing filler, such as calcium carbonate. An example of a treated calcium carbonate is WINNOFIL® SPM commercially available from Solvay Chemicals.

In another embodiment of the present invention, the catalyst paste includes a reinforcing hydrophobic filler, such as hydrophobic fumed silica. An example of a hydrophobic fumed silica is AEROSIL® R202 commercially available from Degussa Corp. In a further embodiment, the catalyst paste may also include a non-reinforcing filler, such as talc. An example of a talc is TALCRON® MP 30-36 commercially available from Specialty Minerals, Inc.

In yet another embodiment, the base paste includes a reinforcing hydrophilic filler and the catalyst paste includes a reinforcing hydrophobic filler. In a still further embodiment, each of the base paste and catalyst paste further include a non-reinforcing filler.

EXAMPLES

A dental impression material in accordance with the present invention is set forth in Table 1, wherein the material was made from a two-part composition with a base paste: catalyst paste ratio of 5:1.

TABLE 1

|  | Parts |
| --- | --- |
| Base |  |
| UPE norbornenecarboxylate[1] | 29.9 |
| Alkoxy-SPE norbornenecarboxylate[2] | 10.9 |
| CITROFLEX ® A4 plasticizer (Morflex) | 13.6 |
| Siloxane norbornenecarboxylate[3] | 1.6 |
| HDK ® N20P Hydrophilic Fumed Silica (Wacker Silicones) | 5 |
| WINNOFIL ® SPM coated Calcium carbonate (Solvay) | 39 |
| Catalyst |  |
| CITROFLEX ® A4 plasticizer (Morflex) | 51.86 |
| AEROSIL ® R202 Hydrophobic Fumed Silica (Degussa) | 15 |
| TALCRON ® MP 30-36 Talc (Specialty Minerals) | 33 |
| Ruthenium carbene complex 3-1 (1.4 mg/g) | 0.14 |

[1]Compound 3d as disclosed in U.S. patent application No. 11/276,270.
[2]Produced by the following method: 1198.1 g of an EO-PO, EO tipped, polyether diol (Bayer, MULTRANOL ® 9111, MW 4000, 800 cps) and 128.9 g of HPNBC were placed in a jacketed 2 L reactor under a nitrogen atmosphere. It was stripped in vacuum at 100° C. for 1 hour with a vacuum below 30 mbar under moderate stirring. Then the temperature was lowered to 90° C. and 0.985 g of the catalyst B(C$_6$F$_5$)$_3$ was added under a stream of nitrogen. 673.0 g of a hydrogen-terminated polysiloxane (Gelest, DMS-H11, MW 1000-1100, 7-10 cps, SiH = 2.1 mmol/g) were added under vigorous stirring at an addition rate of ca. 10 mL/min. Hydrogen gas evolution was observed through a silicone oil bubbler. It was stirred for another hour and then the Si—H disappearance was monitored by IR. When no more Si—H stretch (ca. 2170 cm$^{-1}$) could be found, the reaction was stopped. When Si—H was still detected, a small amount of HPNBC was added and it was again checked by IR after 1 hour. With respect to the formula provided in paragraph 0023 above, PE is polyether, m is about 16 and q is 0-1. The theoretical weight average molecular weight is about 6360.
[3]Produced by the following method: 329.7 g of HPNBC were placed in a jacketed 2 L reactor under a nitrogen atmosphere. The temperature was raised to 90° C. and 0.819 g of the catalyst B(C$_6$F$_5$)$_3$ was added under a stream of nitrogen. 800 g of tethered hydrosiloxane (Gelest, HMS-151, MW 1900-2000, 30 cps, SiH = 2.1 mmol/g) were added under vigorous stirring at an addition rate of ca. 10 mL/min. Hydrogen gas evolution was observed through a silicone oil bubbler. It was stirred for another hour and then the Si—H disappearance was monitored by IR. When no more Si—H stretch (ca. 2170 cm$^{-1}$) could be found, the reaction was stopped. When Si—H was still detected, a small amount of HPNBC was added and it was again checked by IR after 1 hour. With respect to the formula provided in paragraph 0026 above, the resin has a pendant structure, PE is polyether, m is about 4, and n is about 20. The theoretical weight average molecular weight is about 2734.

The physical properties of the above impression material after it is mixed 5:1 by volume are shown in Table 2. All the properties of ISO specification 4823 are satisfied.

TABLE 2

| Reference | IMPREGUM® Soft QS HB 5:1 (3M ESPE) | P2 MAGNUM 360® (Kulzer) | Present Invention |
|---|---|---|---|
| WT/ST (sec) | 108/225 | 58/122 | 84/243 |
| Shore A (15 +/− 2 min) | 52 (1) | 55 (1) | 55 (1) |
| Shore A (60 +/− 5 min) | 54 (1) | 60 (1) | 62 (1) |
| Shore A (24 +/− 1 hr) | 56 (1) | 65 (1) | 62 (1) |
| Tensile Strength (MPa) | 2.35 (0.22) | 2.9 (0.1) | 3.17 (0.19) |
| Elongation (%) | 254 (34) | 69 (3) | 141 (2) |
| Tear strength (N/mm) | 7.0 (0.1) | 4.2 (0.2) | 5.25 (0.11) |
| Elastic Recovery (%) | 98.8 (0.1) | 99.3 (0.1) | 99.5 (0.1) |
| Strain in Compression | 2.4 (0.3) | 2.6 (0.1) | 2.93 (0.05) |
| Linear Dimensional Shrinkage (%) | 0.4 (0.1) | 0.5 (0.1) | 0.43 (0.03) |
| Detail Reproduction | Good | Good | Good |
| Compatibility with gypsum | Good | Good | Good |
| Consistency (mm) | 33 | 30 | 32 |

The data in Table 2 shows that the dental material curable by ROMP exhibits good properties and is comparable to commercial products. A distinct advantage that the ROMP curable material has is that it is very tolerant to acidic hemostatic agents such as aluminum chloride or aluminum potassium sulfate since it is not dependent on acid for the curing mechanism like the other polyether based impression materials.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention is therefore not limited to the specific details, representative apparatus and method and illustrative examples shown and described. Accordingly, departures may be made from such details without departing from the scope of the general inventive concept.

What is claimed is:

1. A dental impression material comprising:
   (a) a base paste comprising a first base resin and a second base resin, wherein
   (1) the first base resin is an urethane polyester carboxylate backbone or an urethane polyether carboxylate backbone, functionalized with at least two cycloolefin groups capable of undergoing a metathesis reaction, the first base resin having the formula:

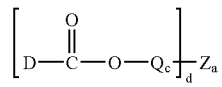

wherein:
a=1-100, c=0 or 1 and d=2-100,
Q is a linear, branched, cyclic or polycyclic organic residue optionally containing siloxane groups (Si—O—Si) and optionally containing heteroatoms selected from the group consisting of B, N, O, Si, P, and S,
Z is a linear, branched, cyclic or polycyclic urethane polyether or urethane polyester optionally containing siloxane groups (Si—O—Si) and optionally containing heteroatoms selected from the group consisting of B, N, O, Si, P, and S, and
D is a cycloolefinic residue and is different than Q or Z; and (2) the second base resin is an alkoxy-siloxane polyester carboxylate backbone or an alkoxy-siloxane polyether carboxylate backbone, functionalized with at least two cycloolefin groups capable of undergoing a metathesis reaction, the second base resin having the formula:

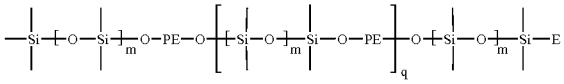

wherein:

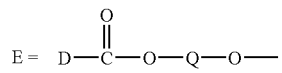

PE is a polyether or polyester fragment,
m=1-500,
q=0-10,
Q is a linear, branched, cyclic or polycyclic organic residue optionally containing siloxane groups (Si—O—Si) and optionally containing heteroatoms selected from the group consisting of B, N, O, Si, P, and S, and
D is a cycloolefinic residue and is different than Q or Z; and (b) a catalyst paste comprising a metal carbene complex catalyst dissolved in a solvent that is miscible with the base paste and capable of initiating the metathesis reaction when the catalyst paste is mixed with the base paste, wherein the catalyst has the structure:

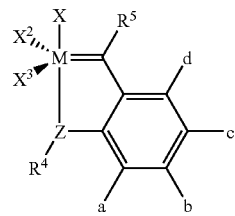

wherein:

M is ruthenium or osmium,

X is an alkylidene ligand with basicity higher than that of tricyclohexylphosphine (PCy$_3$), $X^2$ and $X^3$ are either the same or different and are any anionic ligand, Z is oxygen (O) or sulfur (S), and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

2. The composition of claim 1 wherein the first base resin is a dinorbornenyl dicarboxylate urethane polyester.

3. The composition of claim 1 wherein the first base resin is a dinorbornenyl dicarboxylate urethane polyether.

4. The composition of claim 1 wherein the first base resin has the following structure:

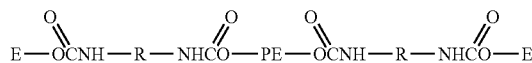

where E=a cycloolefinic endcapper D, R=a diisocyanate fragment, and PE=a polyol.

5. The composition of claim 1 wherein the first base resin is a difunctional urethane polyether carboxylate and the polyether comprises one or more of butylene oxide units, ethylene oxide units or propylene oxide units, or combinations thereof.

6. The composition of claim 1 wherein D is a cycloolefinic residue selected from the group consisting of norbornenyl, norbornenylethyl, cyclopentenyl, 7-oxanorbornenyl, norbornadienyl, and 7-oxanorbornadienyl.

7. The composition of claim 1 wherein the catalyst has the structure:

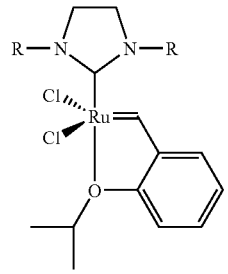

wherein R is mesityl.

8. The composition of claim 1 wherein the first base resin is:

where R hexyl, PE polyether, and

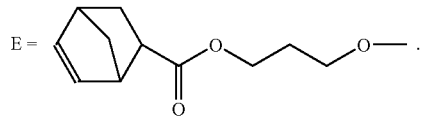

9. The composition of claim 1 wherein, in the second base resin, PE is a polyether containing propylene oxide (PO) and ethylene oxide (EO) fragments, m is about 16, q 0 or 1 and

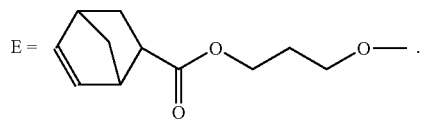

10. The composition of claim 1 wherein, in the second base resin, PE is a polyether containing propylene oxide (PO) and ethylene oxide (EO) fragments, m=1-50, q 0-1 and

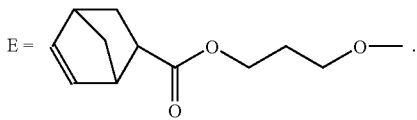

11. The composition of claim 1 wherein the base paste further comprises a third base resin that is a siloxane carboxylate backbone functionalized with at least two cycloolefin groups capable of undergoing a metathesis reaction.

12. The composition of claim 11 wherein the third base resin is a pendant structure having the following formula:

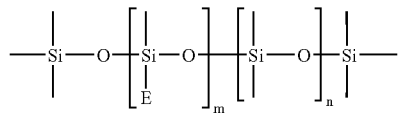

where m=1-50, n=0-200 and

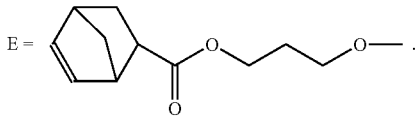

13. The composition of claim 11 wherein the third base resin is a terminated structure having the following formula:

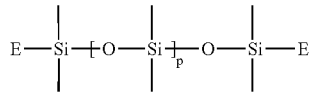

where p=0-200 and

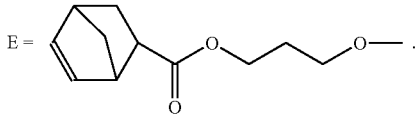

14. The composition of claim 11 wherein the third base resin is a cyclic structure having the following formula:

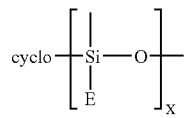

where x=3-6 and

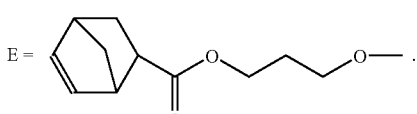

15. The composition of claim 1 wherein the base paste and catalyst paste each further comprise a reinforcing filler and a non-reinforcing filler.

16. The composition of claim 1 wherein the base paste further comprises a hydrophilic filler.

17. The composition of claim 1 wherein the catalyst paste further comprises a hydrophobic filler.

18. The composition of claim 1, wherein the first base resin is

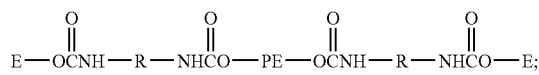

wherein the base paste further comprises a third base resin capable of undergoing a metathesis reaction and selected from at least one of:

a pendant structure having the following formula:

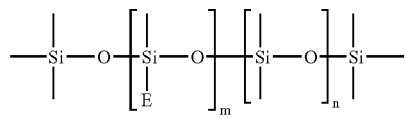

a terminated structure having the following formula:

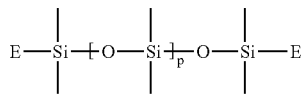

or
a cyclic structure having the following formula:

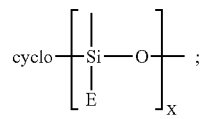

wherein R=a diisocyanate fragment, PE=a polyester or polyether fragment, m=1-50, q=0-1, n=0-200, p=0-200, x=3-6 and E is a cycloolefinic residue selected from the group consisting of norbornenyl, norbornenylethyl, cyclopentenyl, 7-oxanorbornenyl, norbornadienyl, and 7-oxanorbornadienyl; and wherein the base paste further comprises a hydrophilic filler component and the catalyst paste further comprises a hydrophobic filler component.

19. The composition of claim 18 wherein the catalyst has the structure:

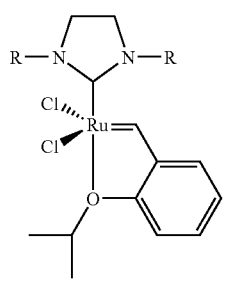

wherein R is mesityl.

20. The composition of claim 18 wherein PE=a polyether containing propylene oxide (PO) and ethylene oxide (EO) fragments and

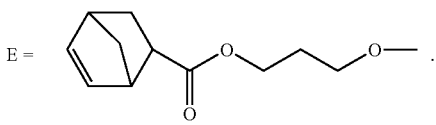

* * * * *

UNITED STATES PATENT AND TRADEMARK OFFICE
CERTIFICATE OF CORRECTION

PATENT NO.      : 7,625,551 B2
APPLICATION NO. : 11/276273
DATED           : December 1, 2009
INVENTOR(S)     : Christos Angeletakis Page 1 of 2

It is certified that error appears in the above-identified patent and that said Letters Patent is hereby corrected as shown below:

Col. 3, line 25, " 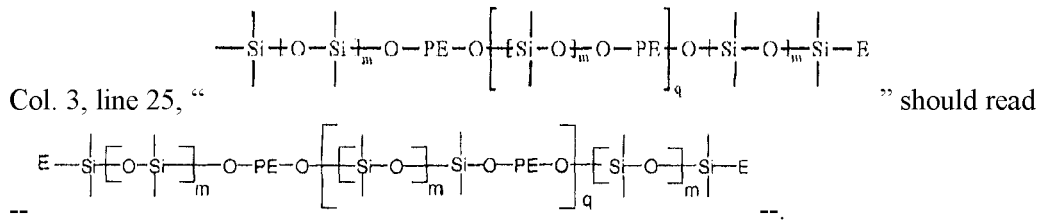 " should read -- --.

Col. 8, line 48, " 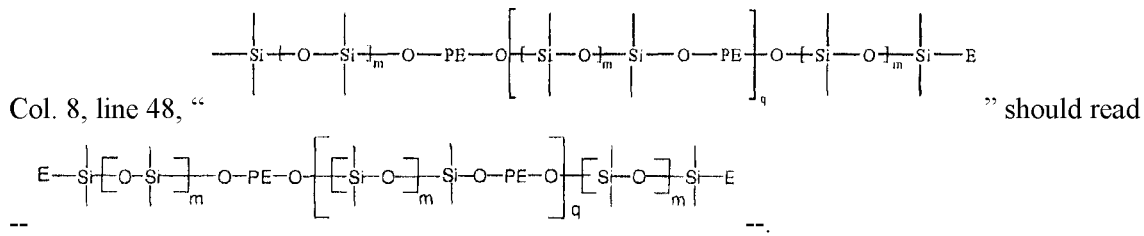 " should read -- --.

Col. 13, line 44, claim 1, "resin is an urethane" should read --resin is a urethane--.

Col. 13, line 45, claim 1, "backbone or an urethane" should read --backbone or a urethane--.

Col. 14, line 10, " 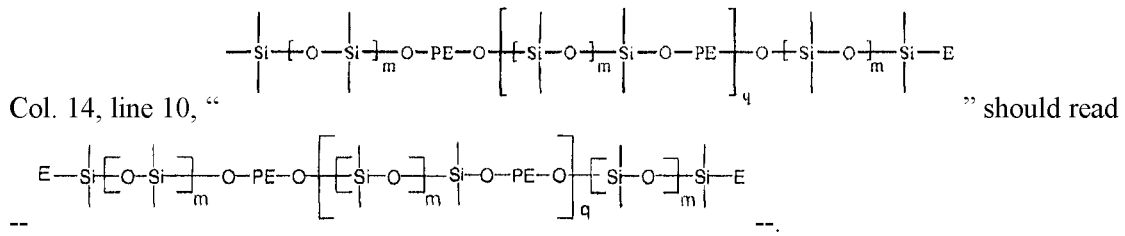 " should read -- --.

Col. 15, line 45, claim 8, "R hexyl, PE polyether" should read --R=hexyl, PE=polyether--.

Signed and Sealed this

Twenty-seventh Day of April, 2010

David J. Kappos
*Director of the United States Patent and Trademark Office*

Col. 15, line 56, claim 9, "q 0 or 1" should read --q=0 or 1--.

Col. 15, line 67, claim 10, "q 0-1" should read --q=0-1--.

UNITED STATES PATENT AND TRADEMARK OFFICE
CERTIFICATE OF CORRECTION

PATENT NO. : 7,625,551 B2 Page 1 of 1
APPLICATION NO. : 11/276273
DATED : December 1, 2009
INVENTOR(S) : Christos Angeletakis It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 887 days.

Signed and Sealed this

Second Day of November, 2010

David J. Kappos
*Director of the United States Patent and Trademark Office*